(12) United States Patent
Banik et al.

(10) Patent No.: US 11,471,610 B1
(45) Date of Patent: Oct. 18, 2022

(54) ASYMMETRICAL CLOSURE FOR A MEDICAL DEVICE

(71) Applicants: Robert Banik, Hollywood, FL (US); Jonathan J. Vitello, Ft. Lauderdale, FL (US)

(72) Inventors: Robert Banik, Hollywood, FL (US); Jonathan J. Vitello, Ft. Lauderdale, FL (US)

(*) Notice: Subject to any disclaimer, the term of this patent is extended or adjusted under 35 U.S.C. 154(b) by 179 days.

(21) Appl. No.: 16/657,769

(22) Filed: Oct. 18, 2019

Related U.S. Application Data

(63) Continuation-in-part of application No. 29/704,234, filed on Sep. 3, 2019, now Pat. No. Des. 948,713.

(60) Provisional application No. 62/747,475, filed on Oct. 18, 2018.

(51) Int. Cl.
A61M 5/32 (2006.01)

(52) U.S. Cl.
CPC ..... *A61M 5/3202* (2013.01); *A61M 2209/084* (2013.01)

(58) Field of Classification Search
CPC ................ A61M 39/20; A61M 5/3202; A61M 2005/3104; A61M 2005/312; A61B 5/150351; B65D 1/00
See application file for complete search history.

(56) References Cited

U.S. PATENT DOCUMENTS

| 722,943 A | 3/1903 | Chappell |
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,489,268 A | 1/1970 | Meierhoefer |

(Continued)

FOREIGN PATENT DOCUMENTS

| EP | 0148116 | 7/1985 |
| GB | 486367 | 6/1938 |

(Continued)

OTHER PUBLICATIONS

Arai Tsugio, Pilfering Proof Cap, Jan. 1, 1996.

*Primary Examiner* — Laura A Bouchelle
(74) *Attorney, Agent, or Firm* — Malloy & Malloy, PL; Jennie S. Malloy; Peter A. Matos

(57) ABSTRACT

A closure for a medical device includes a base having a terminal end for supporting the base in an upright orientation. A connector is mounted on the base for the attachment to the medical device. Automatic, self-righting capabilities of the closure include a curved, substantially bulbous, exterior surface of the base and a center of mass located between the terminal end and a flange. The flange is connected to the base and includes a multi-level peripheral edge extending outwardly from said base at different distances. An included asymmetrical structure of the closure facilitates the automatic, self-righting capabilities thereof.

13 Claims, 5 Drawing Sheets

(56) References Cited

U.S. PATENT DOCUMENTS

| | | |
|---|---|---|
| 3,568,673 A | 3/1971 | Cowley |
| 3,574,306 A | 4/1971 | Alden |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,726,445 A | 4/1973 | Ostrowsky et al. |
| 3,747,751 A | 7/1973 | Miller et al. |
| 3,850,329 A | 11/1974 | Robinson |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,742,910 A | 5/1988 | Staebler |
| 4,743,229 A | 5/1988 | Chu |
| 4,743,231 A | 5/1988 | Kay et al. |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A | 6/1991 | Bolton |
| 5,049,129 A | 9/1991 | Zdeb et al. |
| 5,057,093 A | 10/1991 | Clegg et al. |
| D323,392 S | 1/1992 | Byrne |
| 5,085,332 A | 2/1992 | Gettig et al. |
| 5,090,564 A | 2/1992 | Chimienti |
| 5,135,496 A | 8/1992 | Vetter et al. |
| 5,163,922 A | 11/1992 | McElveen, Jr. et al. |
| 5,165,560 A | 11/1992 | Ennis, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Demark |
| 5,328,474 A | 7/1994 | Raines |
| 5,356,380 A | 10/1994 | Hoekwater et al. |
| 5,370,226 A | 12/1994 | Gollobin et al. |
| 5,380,295 A | 1/1995 | Vacca |
| 5,402,887 A | 4/1995 | Shillington |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,474,178 A | 12/1995 | DiViesti et al. |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,617,954 A | 4/1997 | Kato et al. |
| 5,624,402 A | 4/1997 | Imbert |
| 5,662,233 A | 9/1997 | Reid |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,926,922 A | 7/1999 | Stottle |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A | 9/1999 | Nishida et al. |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,216,885 B1 | 4/2001 | Guillaume |
| 6,279,746 B1 | 4/2001 | Hussaini et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 | 3/2002 | Shapeton et al. |
| 6,375,640 B1 | 4/2002 | Teraoka |
| 6,394,983 B1 | 5/2002 | Mayoral et al. |
| 6,439,276 B1 | 8/2002 | Wood et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanly et al. |
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |

(56) References Cited

U.S. PATENT DOCUMENTS

| | | |
|---|---|---|
| 6,942,643 B2 | 9/2005 | Eakins et al. |
| 7,036,661 B2 | 5/2006 | Anthony et al. |
| 7,055,273 B2 | 6/2006 | Roshkoff |
| 7,100,771 B2 | 9/2006 | Massengale et al. |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,497,330 B2 | 3/2009 | Anthony et al. |
| 7,503,453 B2 | 3/2009 | Cronin et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,886,908 B2 | 2/2011 | Farrar et al. |
| 7,918,830 B2 | 4/2011 | Langan et al. |
| 7,922,213 B2 | 4/2011 | Werth |
| 8,034,041 B2 | 10/2011 | Domkowski et al. |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,413,811 B1 | 4/2013 | Arendt |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,082,157 B2 | 7/2015 | Gibson |
| 9,101,534 B2 | 8/2015 | Bochenko |
| D738,495 S | 9/2015 | Strong et al. |
| 9,125,976 B2 | 9/2015 | Uber, III et al. |
| D743,019 S | 11/2015 | Schultz |
| 9,199,042 B2 | 12/2015 | Farrar et al. |
| 9,199,749 B1 | 12/2015 | Vitello et al. |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S * | 6/2016 | Ingram .................. D9/453 |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Ingram et al. |
| D777,903 S | 1/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh |
| D831,201 S | 10/2018 | Holtz et al. |
| D834,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,315,808 B2 | 6/2019 | Taylor et al. |
| 10,376,655 B2 | 8/2019 | Pupke et al. |
| D859,125 S | 9/2019 | Weagle et al. |
| 10,478,262 B2 | 11/2019 | Niese et al. |
| 10,758,684 B1 | 9/2020 | Vitello et al. |
| 10,773,067 B2 | 9/2020 | Davis et al. |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 | 3/2021 | Hunt et al. |
| 11,040,149 B1 | 6/2021 | Banik |
| 11,040,154 B1 | 6/2021 | Vitello et al. |
| 11,097,071 B1 | 8/2021 | Hunt et al. |
| 11,278,681 B1 | 3/2022 | Banik et al. |
| D948,713 S | 4/2022 | Banik |
| 11,357,588 B1 | 6/2022 | Vitello et al. |
| 11,413,406 B1 | 8/2022 | Vitello et al. |
| 2001/0003150 A1 | 6/2001 | Imbert |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0046962 A1 | 4/2002 | Vallans et al. |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0104770 A1 | 8/2002 | Shapeton et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2004/0008123 A1 | 1/2004 | Carrender et al. |
| 2004/0064095 A1 | 4/2004 | Vitello |

(56) References Cited

U.S. PATENT DOCUMENTS

| | | |
|---|---|---|
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0303267 A1 | 12/2008 | Schnell et al. |
| 2008/0306443 A1 | 12/2008 | Neer et al. |
| 2009/0084804 A1 | 4/2009 | Caspary et al. |
| 2009/0099552 A1 | 4/2009 | Levy et al. |
| 2009/0149815 A1 | 6/2009 | Kiel et al. |
| 2009/0166311 A1 | 7/2009 | Claessens |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0018536 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0182686 A1 | 7/2015 | Okihara |
| 2015/0191633 A1 | 7/2015 | De Boer et al. |
| 2015/0246185 A1 | 9/2015 | Heinz |
| 2015/0302232 A1 | 10/2015 | Strassburger et al. |
| 2015/0305982 A1 | 10/2015 | Bochenko |
| 2015/0310771 A1 | 10/2015 | Atkinson et al. |
| 2016/0067422 A1* | 3/2016 | Davis .................. A61M 5/3202 604/192 |
| 2016/0090456 A1 | 3/2016 | Ishimaru et al. |
| 2016/0136352 A1 | 5/2016 | Smith et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitelio et al. |
| 2016/0250420 A1 | 9/2016 | Maritan et al. |
| 2016/0279032 A1 | 9/2016 | Davis |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1 | 8/2017 | Glaser et al. |
| 2017/0239141 A1 | 8/2017 | Davis et al. |
| 2017/0319438 A1 | 11/2017 | Davis et al. |
| 2017/0354792 A1 | 12/2017 | Ward |
| 2018/0001540 A1 | 1/2018 | Byun |
| 2018/0014998 A1 | 1/2018 | Yuki et al. |
| 2018/0078684 A1 | 3/2018 | Peng et al. |
| 2018/0089593 A1 | 3/2018 | Patel et al. |
| 2018/0098915 A1 | 4/2018 | Rajagopal et al. |
| 2019/0388626 A1 | 12/2019 | Okihara |
| 2022/0008645 A1 | 1/2022 | Ukai et al. |

FOREIGN PATENT DOCUMENTS

| | | |
|---|---|---|
| JP | 08002544 | 1/1996 |
| KR | 101159987 | 6/2012 |
| WO | WO2008000279 | 1/2008 |
| WO | WO2017086607 | 5/2015 |

\* cited by examiner

ASYMMETRICAL CLOSURE FOR A MEDICAL DEVICE

CLAIM OF PRIORITY

The present Non-Provisional patent application claims priority pursuant to 35 U.S.C. Section 119(e) to a currently pending Provisional patent application, namely, that having Ser. No. 62/747,475 filed on Oct. 18, 2018, and further, claims priority to a currently pending design patent application having Ser. No. 29/704,234 filed on Sep. 3, 2019, with the contents of both prior applications being incorporated herein by reference in their entireties.

BACKGROUND OF THE INVENTION

Field of the Invention

A closure for a medical device such as, but not limited to, a syringe, including automatic self-righting capabilities facilitated by, but not limited to, an asymmetrical structure of the closure.

Description of the Related Art

In the manufacturing process for different types of medical devices, there can often be a step which requires careful alignment of the different components thereof, in order to establish a proper assembly. When a medical device is being produced and assembled which involves one or more small components, it is often advantageous to randomly disperse these small components on a working surface and to manually orient and align compatible components which are to be connected to one another.

However, in an environment where sterility is to be maintained, it is not always feasible to manually handle all of the various small components which are to be assembled. This is because manual contact or engagement of the type described can cause contamination of the entire system. Therefore, it would be helpful if one or more medical components which are to be assembled during production had some ability, upon being dispersed onto a work surface, to be oriented in a desired position automatically, so as to assist with the assembly procedure. If developed with an ability to automatically assume a desired position, it should help to maintain the sterility of such components by eliminating or reducing the amount of manual contact needed for assembly.

Accordingly, there is a need in the industry associated with the manufacture, assembly. packaging and use of medical components to address the problems associated with the assembly of such components, while helping to maintain the sterility of the resulting assembled medical device.

SUMMARY OF THE INVENTION

The present invention is directed to a closure for a medical device and may include, but is not limited to, a tip cap of the type connected to the discharge port of a syringe. However, as will be apparent from the discussion which follows, the structural and operative features of the one or more embodiments of the closure may be modified for operative connection with different medical devices, other than a syringe, and yet would still fall within the intended spirit and scope of the present invention.

In more specific terms, the closure comprises a base including a terminal end which is dimensioned and configured to support the base in an upright orientation. As explained in greater detail hereinafter, the intended and preferred "upright orientation" will position the closure such that a connector associated therewith will be disposed in an exposed and readily accessible position for attachment to the connector structure of the intended medical device.

As such, the connector is mounted on the base in a substantially opposite disposition to the terminal end and is configured for attachment to a compatible connector structure of the medical device. By way of nonlimiting example, the connector associated with the closure may be structured as, but not limited to, an enteral connector; an oral connector; a Lure slip connector; a Luer lock connector or a neuraxial connector.

In addition, a flange is connected to the base in substantially opposing relation to the terminal end and in at least partially surrounding relation to the connector. Further, the flange may be integrally attached adjacent to or alternatively, contiguous with the correspondingly disposed periphery of the base, at a connecting junction therebetween. Moreover, the flange may extend outwardly and/or upwardly therefrom, in surrounding relation to the connector. The flange may also include an outer peripheral edge having a curved, sloping configuration at least partially defined by a plurality of edge segments, some of which are located at different levels by being outwardly spaced from the base at different distances.

Additional operative features of the inventive closure include, in various embodiments, a "self-righting" structure which serves to "automatically" dispose the closure in the aforementioned upright orientation while being supported on the terminal end of the base. Such self-righting capabilities provide for the closure (and/or a plurality of such closures) to assume the aforementioned upright orientation when they are freely dropped or dispersed on a substantially level or horizontal a supporting surface and/or work surface. In other words, the "self-righting" structure of the inventive closure allows for the upright orientation of the closure to be assumed automatically, without manual or mechanical manipulation or contact.

Accordingly, the self-righting structure of the closure further comprises a base structured to locate a center of mass for or on the closure, between the terminal end and the connecting junction between the base and the flange.

With the center of mass being so located, the self-righting structure of the closure further includes the base having a curved, substantially bulbous exterior surface configuration extending continuously from the terminal end to the connecting junction between the flange and the base. In addition, the self-righting structure may further comprise a flange having the curved, substantially sloping, peripheral edge, including the peripheral edge being at least partially defined by a plurality of edge segments being disposed at different levels or spaced distances from the base. Moreover, in at least one embodiment, the different levels of the plurality of edge segments may be continuously, successively and integrally connected to one another along the length of the peripheral edge. However, it is contemplated to be within the spirit and scope of the present invention that the plurality of edge segments may be at least partially segmented or separated from one another.

In addition, the one or more embodiments of the closure of the present invention include an asymmetrical structure. As explained in greater detail hereinafter, the asymmetrical structure may further enhance the self-righting capabilities. More specifically, the asymmetrical structure comprises the dimensioning and configuring of the exterior of the closure in a manner which effectively eliminates any location or area on the exterior thereof, other than the terminal end, that can support the closure, unless it is in the aforementioned upright orientation.

Therefore, the asymmetrical structure comprises at least two opposing portions and/or peripheral edge segments of the flange being disposed on opposite sides of the center of mass of the closure, which extend outwardly from the base at different distances and have different configurations. In addition, the asymmetrical structure may also comprise at least two opposing portions of the curved, substantially bulbous exterior surface of the base, which may also be disposed on opposite sides of the center of mass of the closure and/or have different sizes, and include different outer curved surface configurations.

As set forth above, one embodiment of the closure includes a terminal end being dimensioned and configured to support the closure in the preferred upright orientation. As such, the configuration of the terminal end is substantially or sufficiently level and/or planar to facilitate the intended support on a substantially level or horizontal supporting surface.

However, one additional embodiment of the closure includes a structural modification of the terminal end to include and/or at least partially define a non-rotational connection. The non-rotational connection facilitates the removable connection or attachment of the closure and/or a plurality of such closures, to a supporting platform in the upright orientation. Further, the supporting platform to which the one or more closures may be removably attached, in a rotationally restrictive manner, may be the floor or bottom portion of a container used for packaging the closures. The rotationally restrictive, but removable attachment of the closures to the support platform/container facilitates their connection to the intended medical device in a manner which eliminates the necessity of touching the closures to accomplish such medical device connection, thereby preserving sterility when required.

Therefore, in at least one preferred embodiment, the closure comprises the terminal end of the base including an inwardly disposed recess and including an inner peripheral sidewall or surface. The recess in the terminal end includes a plurality of projections or ribs disposed on the internal sidewall or peripheral surface that extend outwardly, but within the recess, towards a center of the recess. For example, the plurality of ribs may be disposed in spaced relation to one another at a predetermined distance, such as being equally spaced. The recessed end, including the plurality of projections or ribs and the spacing therebetween are cooperatively and correspondingly dimensioned and configured to the exterior of each of a plurality of outwardly extending retaining members formed on a floor of a container, or other support platform to which one or more closures may be removably but non-rotationally attached. Further, as described in greater detail hereinafter, the various embodiments of the closure overcome the recognized problems associated with the manufacture, assembly, packaging and other processing of closures for medical devices.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts of the several views of the drawings.

DETAILED DESCRIPTION OF THE PREFERRED EMBODIMENT

Figure 1:
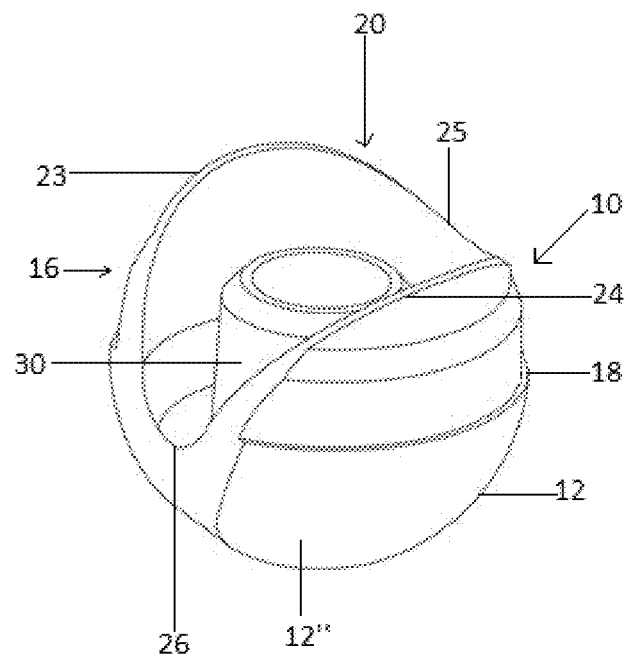
FIG. 1 is a front perspective view of one embodiment of the closure of the present invention.
Figure 2:
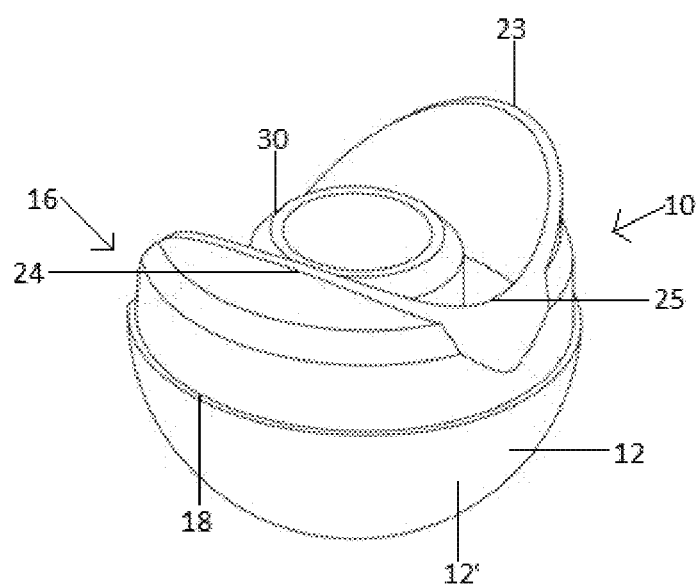
FIG. 2 is a rear perspective view of the embodiment of FIG. 1.
Figure 3:
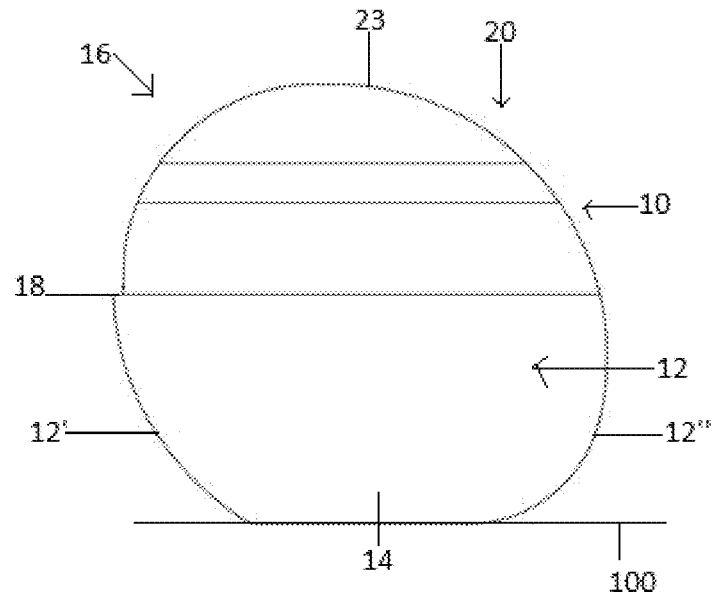
FIG. 3 is a side view of the embodiment of FIGS. 1 and 2.

As represented in the accompanying drawings and with initial reference to the embodiment of FIGS. 1-4, the present invention is directed to a closure, as generally indicated at 10 including a base 12 having a terminal end 14.

In addition, the closure 10 includes a flange generally indicated as 16 connected to the base 12 and extending outwardly therefrom in substantially opposing relation to the terminal end 14. As also represented, the flange 16 is preferably integrally secured to the base 12 at a connecting junction 18, such that the lower or inner end of the flange 16 is secured at the connecting junction 18 adjacent and/or contiguous to the outer periphery of the base 12.

The flange 16 includes an outer or upper peripheral edge, generally indicated as 20, which is disposed and dimensioned to extend outwardly from the base 12 in at least partially surrounding relation to a connector generally indicated as 30. As also represented, the outer peripheral edge 20 comprises a curved, at least partially sloping configuration along its length. Such a sloping structure or configuration comprises a plurality of curved edge segments 23-26, preferably disposed in continuously successive, integral attachment to one another. In more specific terms, the plurality of segments of the curved, sloping peripheral edge 20 include two upper or outermost edge segments 23 and 24, an intermediate edge segment 25 and a lower edge segment 26. As also represented, the lower edge segment 26 at least partially defines an open side or end of the flange 16, which is disposed in open communication with the interior of the flange and a connector 30.

Therefore, the curved, sloped configuring of the outer peripheral edge 20 comprises at least some of the plurality of edge segments 23-26 disposed at different levels or at different outwardly spaced distances from the base 12 and/or the connecting junction 18 between the base 12 and the flange 16, which would make it impossible for the closure to be supported on any portion of the outer peripheral edge 20 of the flange 16. This feature further enhances and at least partially defines the self-righting characteristics of the closure 10.

Figure 4:
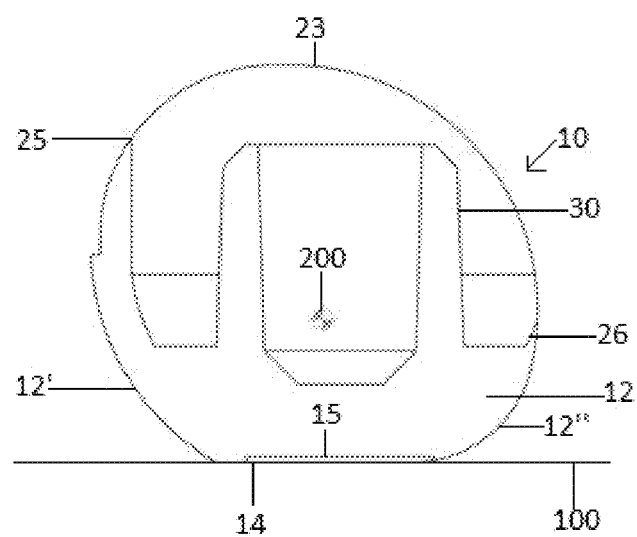
FIG. 4 is a transverse sectional view of FIG. 3 representing the interior thereof.
Figure 5:
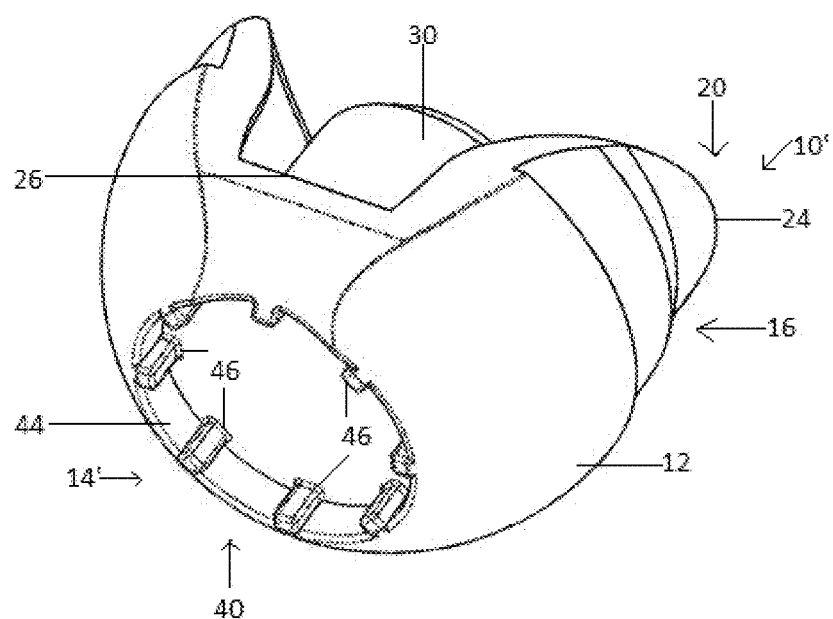
FIG. 5 is a bottom perspective view of another embodiment of the closure of the present invention.
Figure 6:
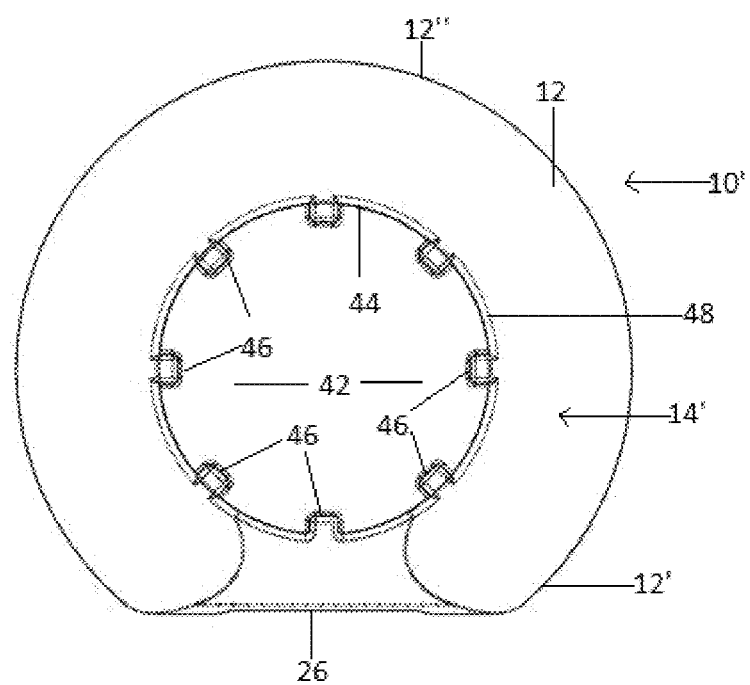
FIG. 6 is a bottom plan view of the embodiment of FIG. 5.

It is to be noted that the terms "upper", "lower", "outer", etc. refer to the location or disposition of the indicated component of the closure 10 when it is supported by the terminal end 14 in the preferred "upright orientation," as represented in at least FIGS. 4 and 5.

With further regard to the connector 30, it is disposed at least partially on the interior of the flange 16 and in at least partially surrounded relation by the flange 16. The connector 30 is cooperatively configured and structured to facilitate attachment to a connector structure associated with an intended medical device such as, but not limited to, a medical syringe. Therefore, by way of non-limiting example, the connector 30 may be structured as an enteral connector; an oral connector; a Lure slip connector; a Luer lock connector; a neuraxial connector or other customized connector configuration compatible with the medical device to which it is intended to be attached.

Additional operative features of the different embodiments of the closure include "self-righting" capabilities accomplished through the provision of a "self-righting" structure on or otherwise associated with the cover 10. As intended to be understood, the self-righting capabilities of the cover 10 serves to "automatically" dispose the closure 10 in the aforementioned upright orientation, while being supported in a stable manner by the terminal end 14 of the base 12 on a supporting surface 100, as represented in at least FIGS. 3 and 4. Such "self-righting" capabilities enable the closure 10 and/or a plurality of such closures to "automatically" assume the aforementioned upright orientation when they are freely dropped or dispersed on the supporting surface 100, or work surface, which is substantially, but not necessarily precisely, level or horizontal. As such, the upright orientation of the closure 10 on the supporting surface 100 will be assumed without manual or mechanical manipulation or contact.

The self-righting structure of the closure 10 further comprises structuring the base 12 to locate a center of mass, schematically represented as 200 in FIG. 4, on the closure 10, between the terminal end 14 and the connecting junction 18. With the center of mass 200 being so located, the self-righting structure of the closure further includes the base 12 having the curved, substantially bulbous, exterior surface configuration, as represented throughout the accompanying Figures. As also represented, in at least one embodiment the curved, substantially bulbous, exterior surface of the base 12 extends continuously from the terminal end 14 to the connecting junction 18 between the flange 16 and the base 12.

In addition, and as indicated herein, the self-righting structure may further comprise the curved, at least partially sloping configuration of the outer peripheral edge 20, being at least partially defined by the plurality of edge segments 23-26, disposed at different levels or spaced distances from the base 12 and/or connecting junction 18.

Yet additional structural and operative features of the one or more embodiments of the closure 10 of the present invention include an asymmetrical structure. Moreover, the structuring of the closure 10 to include the asymmetrical structure may further enhance the self-righting capabilities. More specifically, the asymmetrical structure generally comprises the dimension and configuration of the exterior of the components or parts of the closure 10 in a manner which effectively eliminates any location or area on the exterior thereof, other than the terminal end, that can support the closure in a stable manner, unless it is in the aforementioned upright orientation.

Therefore, the asymmetrical structure comprises, but is not necessarily limited to, different portions of the curved, substantially bulbous configuration of the exterior surface of the base 12 having different sizes and shapes. More specifically, the external side and interior sectional views of FIGS. 3 and 4 respectively, illustrate the base 12 of closure 10 as having an asymmetrical structure and configuration. The asymmetrical structure includes an exterior surface portion 12' having a different size, configuration and length than that of the exterior surface portion 12", wherein the two substantially opposing exterior surface portions 12' and 12" are located on opposite sides of the center of mass 200.

In cooperation therewith, the asymmetrical configuration may further comprise, but is not limited to, at least two opposing portions of the outer peripheral edge 20, such as edge segments 25 and 26, being located on opposite sides of the center of mass 200 and accordingly, being of different locations, sizes and configurations.

With primary reference to FIGS. 5-9 the present invention includes another embodiment of the closure, generally indicated as 10', which is structurally and operationally equivalent to the closure 10, at least to the extent of including the aforementioned and described self-righting structure and asymmetrical structure. As such, the closure 10' includes self-righting capabilities of the base 12 including the curved, bulbous configuration, which also at least partially defines the asymmetrical structure. In addition, the center of mass 200 is located between the terminal and 14' and the connecting junction 18 of the flange 16. Further, the closure 10' includes the flange 16 connected to the base 12 at the connecting junction 18 and also, includes an outer peripheral edge 20 having the curved, sloping configuration extending continuously along the length thereof. As such, the outer peripheral edge 20 includes the plurality of edge segments 23-26 disposed outwardly from the base 12 and/or the connecting junction 18 at different levels or distances.

Moreover, the aforementioned asymmetrical structure of the closure 10' is at least partially defined by, but not limited to, different portions of the base, as at 12' and 12", being located on opposite sides of the center of mass 200 and being of different sizes, shapes and locations. Further, the aforementioned asymmetrical structure of the closure 10' is at least partially defined by, but not limited to, different portions of the outer peripheral edge 20 of the flange 16 including at least two opposing portions, such as at edge segments 24 and 26 being disposed on different sides of the center of mass 200 and having different sizes, configurations and locations.

However, one structural difference between the embodiments of the closure generally indicated as 10 and 10' include a structural modification of the distal end, generally indicated as 14'. More specifically, the distal end 14' comprises a non-rotational connector, generally indicated as 40. Further, the nonrotational connector 40 comprises a recessed portion 42 extending into the base 12 and including an inner sidewall or inner peripheral surface 44. In addition, a plurality of projections or ribs 46 are integrally or otherwise fixedly secured to the interior peripheral sidewall 44 and extend outwardly therefrom, but within the recess 42, towards a substantial center of the recess 42. The plurality of ribs 46 are disposed in spaced relation to one another about the circumference of the inner peripheral side wall or surface 44, such as being equidistant from one another.

Figure 7:
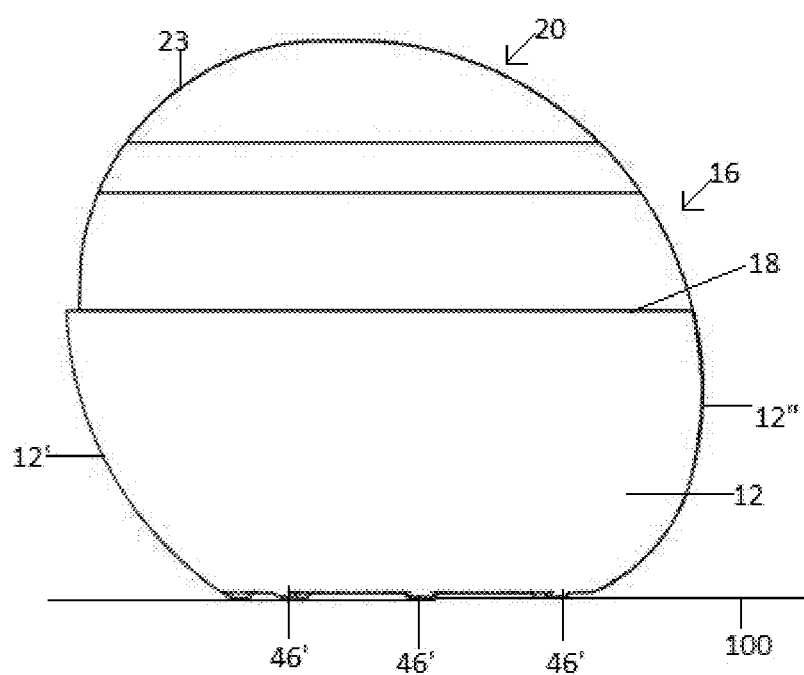
FIG. 7 is a side elevation view of the embodiment of FIGS. 5 and 6.
Figure 8:
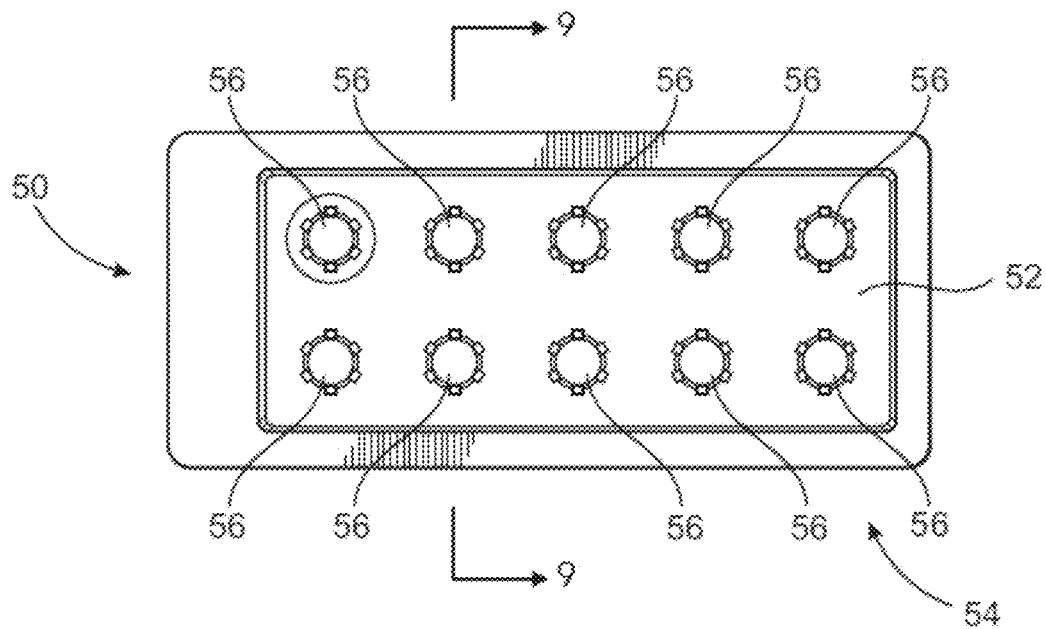
FIG. 8 is a top plan view of a support platform to which one or more of the closures of the embodiment of FIGS. 5-7 may be non-rotationally attached/supported.
Figure 9:
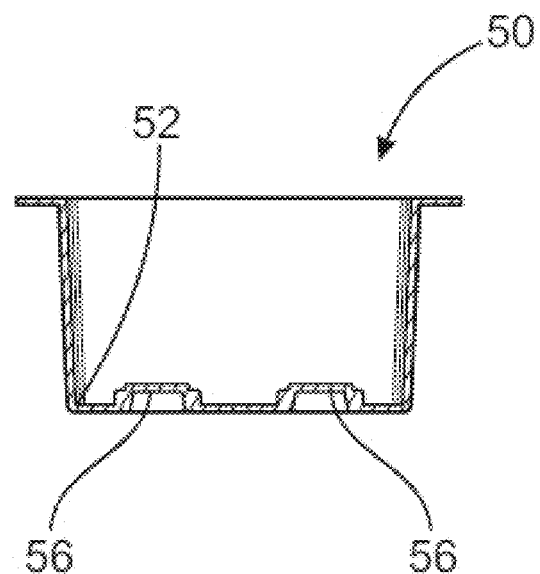
FIG. 9 is a transverse sectional view of the support platform of the embodiment of FIG. 8.

As represented in at least FIG. 7, in one embodiment at least some of the plurality of ribs or projections 46 have outermost ends 46' that may extend at least minimally outwardly from the recess 42. Further, the outwardly extending ends 46' may be disposed in a common plane and thereby define a substantially level configuration for the stable support of the closure 10' on a supporting surface 100 in the aforementioned upright orientation. In contrast, the plurality of ribs or projections 46 may not extend outwardly from the interior of the recess 42. In such a structural modification the outer periphery of the recess, as at 48, may serve as the level, substantially planar portion of the base 12 that supports the remainder of the closure 10 in a stable manner in the preferred upright orientation.

It is to be noted that a comparison of the embodiment of FIG. 4 with that of FIG. 7 indicates that a small indentation 15 may be made in the terminal and 14 to facilitate the molding, manufacture, processing etc. thereof. However, the indentation 15 is not to be confused with the inwardly directed recess 42 in the embodiments of FIGS. 5-7. If such an indentation 15 is present, the surrounding outer periphery of the indentation 15 will be in a common plane and define the substantially level configuration of the end 14, enabling a stable upright orientation of the closure 10 on a supporting surface 100.

With a concurrent consideration of FIGS. 5-6 and 8-9, the non-rotational connector 40 is disposed and structured to establish a removable, but non-rotational connection with a support platform such as, but not limited to, the floor or interior bottom 52 of the container 50. Further, the recessed end 14' including the plurality of projections or ribs 46 and the spacing therebetween are cooperatively and correspondingly dimensioned and configured to the exterior of each of a plurality of outwardly extending retaining members 56 formed on the floor 52 of the container 50.

Each of the retaining members 56 are disposed, dimensioned and configured to correspond to that of the interior of the recess 42 formed in the terminal end 14' of the closure 10'. Due to the corresponding configuration between the recess 42 and the exterior of each of the retaining members 56, each of the one or more closures 10' contained within the interior of the container 50, will be mounted on a different one of the retaining members 56 in a removable, but rotational restricting relation thereto. The preventing or the restricting of the rotation of each of the closures 10' within the interior of the container 50, in the manner described, further facilitates the attachment of each of the closures 10' with a syringe or other medical device to which they are intended to be attached.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A closure for a medical device comprising:
    a base including a terminal end dimensioned and configured to support said base in an upright orientation,
    a connector mounted on said base opposite to said terminal end and configured for attachment to a compatible connector structure of the medical device,
    a flange connected to an outer periphery of said base in at least partially surrounding relation to said connector and including a curved outer peripheral edge having a plurality of edge segments extending outwardly from said base at least partially beyond said connector,
    a self-righting structure comprising said base including an asymmetrical structure,
    said asymmetrical structure comprising a curved, substantially bulbous, exterior surface extending continuously from said terminal end to said flange,
    said curved, substantially bulbous exterior surface including at least two opposing portions disposed on opposite sides of a center of mass and being of different sizes and configurations, and
    said self-righting structure further comprising said center of mass located between said terminal end and said outer periphery of said base.

2. The closure as recited in claim 1 wherein said terminal end comprises a non-rotational connector structured to prevent rotation of said base relative to a supporting platform.

3. The closure as recited in claim 2 wherein said non-rotational connector comprises a recess formed in said base and a plurality of ribs disposed at least partially within said recess.

4. The closure as recited in claim 3 wherein said plurality of ribs are integrally formed on an interior peripheral sidewall of said recess in spaced relation to and independent of said curved, substantially bulbous exterior surface.

5. The closure as recited in claim 4 wherein said plurality of ribs extend at least partially outward from said recess and said curved, substantially bulbous exterior surface in supporting relation to said base, concurrent to said upright orientation.

6. The closure as recited in claim 1 wherein said asymmetrical structure further comprises a central longitudinal axis of said connector disposed offset from a central longitudinal axis of said base.

7. The closure as recited in claim 1 wherein said asymmetrical structure further comprising said plurality of edge segments including two upper edge segments, a lower edge segment and an intermediate edge segment; said lower edge segment and said intermediate segment being oppositely disposed to one another, each between opposite ends of said two upper edge segments.

8. The closure as recited in claim 7 wherein said lower edge segment is disposed outwardly from said base a lesser distance than said two lower edge segments, said two upper edge segments disposed outwardly from said base a greater distance than said lower edge segment, said intermediate segment extending outwardly from said base a distance greater than said lower edge segment and less than said upper edge segment.

9. A closure for a medical device comprising:
    a base including a terminal end dimensioned and configured to support said base in an upright orientation,
    a connector mounted on said base opposite to said terminal end and configured for attachment to the medical device,
    a flange connected to said base above and in at least partially surrounding relation to said connector; said flange including a multi-level peripheral edge extending outwardly from said base at different distances,
    a self-righting structure comprising said base including a curved, substantially bulbous exterior surface and a center of mass located between said terminal end and said flange,
    an asymmetrical structure comprising at least two portions of said base, disposed on opposite sides of said center of mass, including different sizes and exterior surface configurations,
    said base comprising a non-rotational connector structured to restrict rotation of said base relative to a supporting platform and including a recess formed in said terminal end,
    a plurality of ribs disposed within said recess, and
    said plurality of ribs integrally formed on and extending outward from a sidewall of said recess.

10. The closure as recited in claim 9 wherein said asymmetrical structure further comprises said multi-level peripheral edge including a plurality of integrally connected edge segments extending outwardly from said base at different distances.

11. The closure as recited in claim 9 wherein said flange includes an open end disposed in communicating relation with said connector and an interior of said flange.

12. The closure as in claim 9 wherein said asymmetrical structure further comprises said multi-level peripheral edge including at least an upper edge segment, a lower edge segment and an intermediate edge segment, said upper edge segment disposed outwardly from said base a greater distance than said lower edge segment; said intermediate segment and said lower edge segment being oppositely disposed to one another, between different opposite ends of said two upper edge segments.

13. The closure as recited in claim 9 wherein said plurality of ribs extend at least partially outward from said recess and said curved, substantially bulbous exterior surface in supporting relation to said base, concurrent to said upright orientation.

\* \* \* \* \*